United States Patent
Shoji et al.

(10) Patent No.: US 7,147,467 B2
(45) Date of Patent: Dec. 12, 2006

(54) TOOTH MOBILITY MEASURING APPARATUS

(75) Inventors: Shigeru Shoji, Sendai (JP); Masahiro Otsuka, Kawasaki (JP)

(73) Assignee: TOEI Electric Co. Ltd. (JP)

( * ) Notice: Subject to any disclaimer, the term of this patent is extended or adjusted under 35 U.S.C. 154(b) by 498 days.

(21) Appl. No.: 10/616,314

(22) Filed: Jul. 9, 2003

(65) Prior Publication Data

US 2004/0009453 A1    Jan. 15, 2004

(30) Foreign Application Priority Data

Jul. 12, 2002    (JP)    ............................. 2002-204637

(51) Int. Cl.
*A61C 3/00*    (2006.01)
(52) U.S. Cl. ....................................... 433/72
(58) Field of Classification Search ................. 433/72, 433/215, 118, 119, 120, 121, 150, 151; 600/589, 600/590, 553; 33/513, 514; 73/12.01, 12.12, 73/573, 579
See application file for complete search history.

(56) References Cited

U.S. PATENT DOCUMENTS 4,470,810 A * 9/1984 Bourdeau et al. ............. 433/72
4,499,906 A * 2/1985 Wohlgemuth et al. ...... 600/589
5,496,172 A * 3/1996 Albelda et al. ............. 433/120
5,545,038 A * 8/1996 Beebe ......................... 433/120
5,803,730 A * 9/1998 Khademazad et al. ........ 433/72
5,951,292 A * 9/1999 Lee et al. .................... 433/215

FOREIGN PATENT DOCUMENTS

JP    4-279157    10/1992

* cited by examiner

*Primary Examiner*—Todd E. Manahan
(74) *Attorney, Agent, or Firm*—Michael Best & Friedrich LLP

(57) ABSTRACT

A tooth mobility measuring apparatus of this invention includes an impact mechanism which injects or sucks a fluid to apply an impact to a tooth, a sensor which detects the displacement state of the tooth which is moved by the impact force from the impact mechanism, and a tooth mobility calculation mechanism which calculates the tooth mobility of the tooth on the basis of the output signal from the sensor. The displacement state of the tooth is measured without touching the tooth.

20 Claims, 3 Drawing Sheets

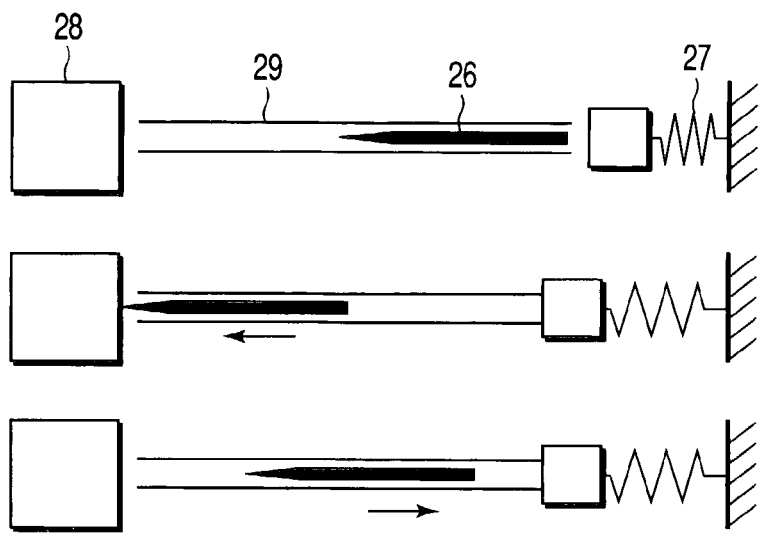
FIG. 2
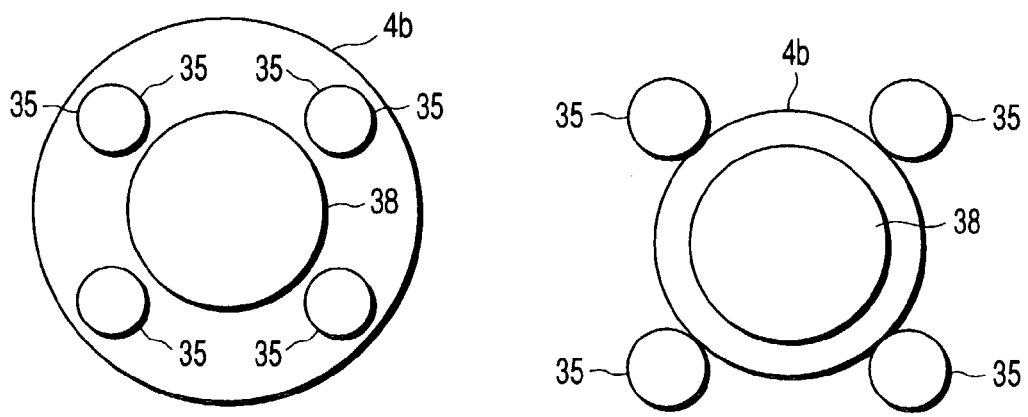
FIG. 4
FIG. 5
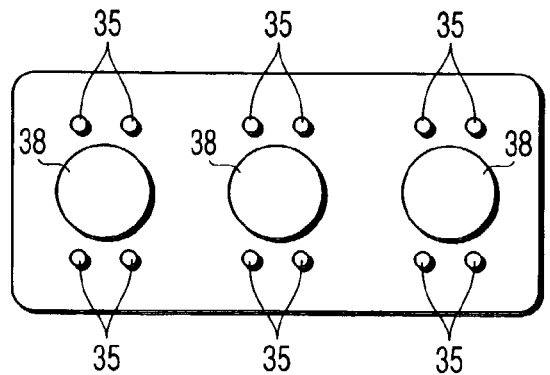
FIG. 6

TOOTH MOBILITY MEASURING APPARATUS

CROSS-REFERENCE TO RELATED APPLICATIONS

This application is based upon and claims the benefit of priority from the prior Japanese Patent Application No. 2002-204637, filed Jul. 12, 2002, the entire contents of which are incorporated herein by reference.

BACKGROUND OF THE INVENTION

1. Field of the Invention

The present invention relates to a tooth mobility measuring apparatus which measures the tooth mobility of a tooth to determine the state of the tooth.

2. Description of the Related Art

Tooth mobility measurement is done to diagnose a tooth and the state of a tooth (e.g., the state of periodontal tissue that supports a tooth). Conventionally, a subjective measuring method has been used in which the tooth mobility is grasped on the basis of inspection, palpation percussion, the moving states of teeth, and the like. This method however largely depends on the subjectivity of the operator. In addition, since this method gives importance to only the displacement amount of a tooth, properties such as the viscoelasticity of periodontal tissue may not be made clear. To objectively determine the tooth mobility, a tooth mobility measuring apparatus disclosed in Jpn. Pat. Appln. KOKAI Publication No. 4-279157 has been developed. As shown in FIG. 1, this tooth mobility measuring apparatus hits a tooth with a hammer 4, catches with a sensor 3 the variation of the tooth that fluctuates upon being hit, extracts the variation as an electrical signal, and calculates the tooth mobility of the tooth on the basis of the electrical signal.

FIG. 2 shows another apparatus. This apparatus causes a pick 26 to fly through a cylinder 29 using the force of a spring 27 to make an impact on a tooth 28.

The conventional measuring apparatus described in Jpn. Pat. Appln. KOKAI Publication No. 4-279157 measures the acceleration of displacement of a tooth. The acceleration is measured by bringing the hammer into direct contact with the tooth, and the tooth mobility is measured on the basis of the acceleration. Hence, for accurate measurement, the hammering position on the tooth must be accurate. In addition, hammering must be done with an appropriate force. If the hammering force is too strong, the patient may feel a pain. The conventional apparatus shown in FIG. 2 executes automatic hammering. For this reason, the magnitude of load is stable, and the hammering force is unlikely to be too strong. However, patients whose teeth and periodontal tissue are not in a good state may feel pain upon hammering. Furthermore, since the acceleration of the hammer changes according to the tilt of the apparatus, the magnitude of load may change and influence the measuring accuracy.

BRIEF SUMMARY OF THE INVENTION

The present invention has been made in consideration of the above situation, and has as its object to provide a tooth mobility measuring apparatus which may measure tooth mobility by achieving at least one of accurately measuring at least one of the displacement and tooth mobility of a tooth without bringing a measuring tool into contact with the tooth and easing the pain felt by a patient. In this specification, the term "tooth" includes an artificial tooth, such as a dental implant, as well as a natural tooth.

According to an aspect of the present invention, there is provided a tooth mobility measuring apparatus comprising: an impact mechanism which has at least one of an injection mechanism having an injection port which injects a fluid and a suction mechanism having a vacuum port which sucks air, and applies an impact force on a tooth by injection or suction, the impact mechanism comprising a control mechanism which sets a pressure by injection or suction to a predetermined value; at least one sensor which detects a displacement state of the tooth which is moved by the impact force of the impact mechanism; and a tooth mobility calculation mechanism which calculates a tooth mobility of the tooth on the basis of an output signal from the sensor.

In this apparatus, the fluid is preferably a gas.

In this apparatus, the gas is preferably air.

In this apparatus, preferably, the injection mechanism or suction mechanism has a nozzle, and the nozzle has a structure adapted to the arrangement and form of the tooth to be inspected.

In this apparatus, the object to be measured simultaneously preferably comprises one or a plurality of teeth.

In this apparatus, the control mechanism may preferably variably adjust the predetermined value.

In this apparatus, the injection mechanism preferably further comprises a temperature adjusting mechanism which adjusts the temperature of the fluid.

In this apparatus, the injection mechanism may preferably adjust at least one of an injection state, a number of times of injection, and an injection timing of the fluid to be impactively injected to the tooth to be inspected.

In this apparatus, the sensor is preferably a measuring device which senses at least one of a change in vibration of air and a change in electrostatic capacitance between the injection port or vacuum port and the tooth surface to detect the displacement state of the tooth.

In this apparatus, the sensor is preferably a measuring device which irradiates the tooth with light and detects the displacement state of the tooth on the basis of reflected light.

In this apparatus, the light of the sensor is preferably a laser beam.

In this apparatus, the light output from the sensor also preferably has a position confirming function to visually recognize a position of a target to be subjected to injection or suction by the impact mechanism.

In this apparatus, the sensor is preferably arranged around the injection port or the vacuum port.

In this apparatus, the displacement state of the tooth to be detected is preferably at least one of a displacement amount and a displacement time of the tooth to be inspected.

In this apparatus, the tooth mobility calculation mechanism preferably calculates an acceleration of displacement of the tooth on the basis of a maximum. displacement amount and a displacement time of the tooth to be inspected.

In this apparatus, the tooth mobility calculation mechanism preferably calculates the tooth mobility of the tooth to be inspected on the basis of at least one of the injection pressure or suction pressure for the tooth, the maximum displacement amount of the tooth, the displacement time of the tooth, and the distance between the injection port or vacuum port of the impact mechanism and the tooth to be inspected.

In this apparatus, the tooth mobility measuring apparatus preferably further comprises at least one of a storage device which stores the calculated tooth mobility, a display mechanism which displays the tooth mobility, and an output mechanism which prints the tooth mobility on a paper sheet.

In this apparatus, the tooth mobility measuring apparatus preferably further comprises means for locating the injection port or the vacuum port with respect to the tooth to be inspected.

According to another aspect of the present invention, there is provided a tooth mobility measuring method comprising steps of: (a) applying an impact force having a predetermined pressure on a tooth to be inspected, the impact force being applied by one of injecting a fluid having a predetermined pressure to the tooth to be inspected and sucking the tooth to be inspected at a predetermined pressure; (b) detecting a displacement state of the tooth which is moved by the impact force; and (c) calculating a tooth mobility of the tooth on the basis of the detected displacement state.

In this measuring method, the fluid in the step (a) is preferably a gas.

In this measuring method, the gas in the step (a) is preferably air.

In this measuring method, the step (a) preferably further comprises a step of adjusting the pressure of the fluid.

In this measuring method, the step (a) preferably further comprises a step of adjusting the temperature of the fluid.

In this measuring method, the step (b) preferably comprises a step of adjusting at least one of a stress form of the impact, a number of times of impact, and a timing of application of the impact force.

In this measuring method, the step (a) preferably further comprises a step of locating an injection port or a vacuum port to a predetermined position using means for locating the injection port or the vacuum port with respect to the tooth to be inspected.

In this measuring method, the step (b) preferably comprises a step of irradiating the tooth with light and detecting the displacement state of the tooth on the basis of reflected light.

In this measuring method, the step (b) preferably comprises a step of detecting the displacement state of the tooth from at least one of a displacement amount and a displacement time of the tooth to be inspected.

In this measuring method, the step (c) preferably comprises a step of calculating the acceleration of displacement of the tooth to be inspected on the basis of the maximum displacement amount of the tooth and the displacement time of the tooth.

In this measuring method, the step (c) preferably comprises a step of calculating the tooth mobility of the tooth to be inspected on the basis of at least one of the impact force applied to the tooth, a maximum displacement amount of the tooth, a displacement time of the tooth, and a distance between an injection port or a vacuum port and the tooth to be inspected.

In this measuring method, the step (c) preferably comprises at least one of a step of storing the calculated tooth mobility, a step of displaying the tooth mobility, and a step of outputting the tooth mobility to a paper sheet.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a view showing the principle of another conventional tooth mobility measuring apparatus;

FIG. 4 is a front view of an injection port at a nozzle distal end portion;

FIG. 5 is a front view at another nozzle distal end portion; and

FIG. 6 is a front view at still another nozzle distal end portion.

DETAILED DESCRIPTION OF THE INVENTION

Figure 1:
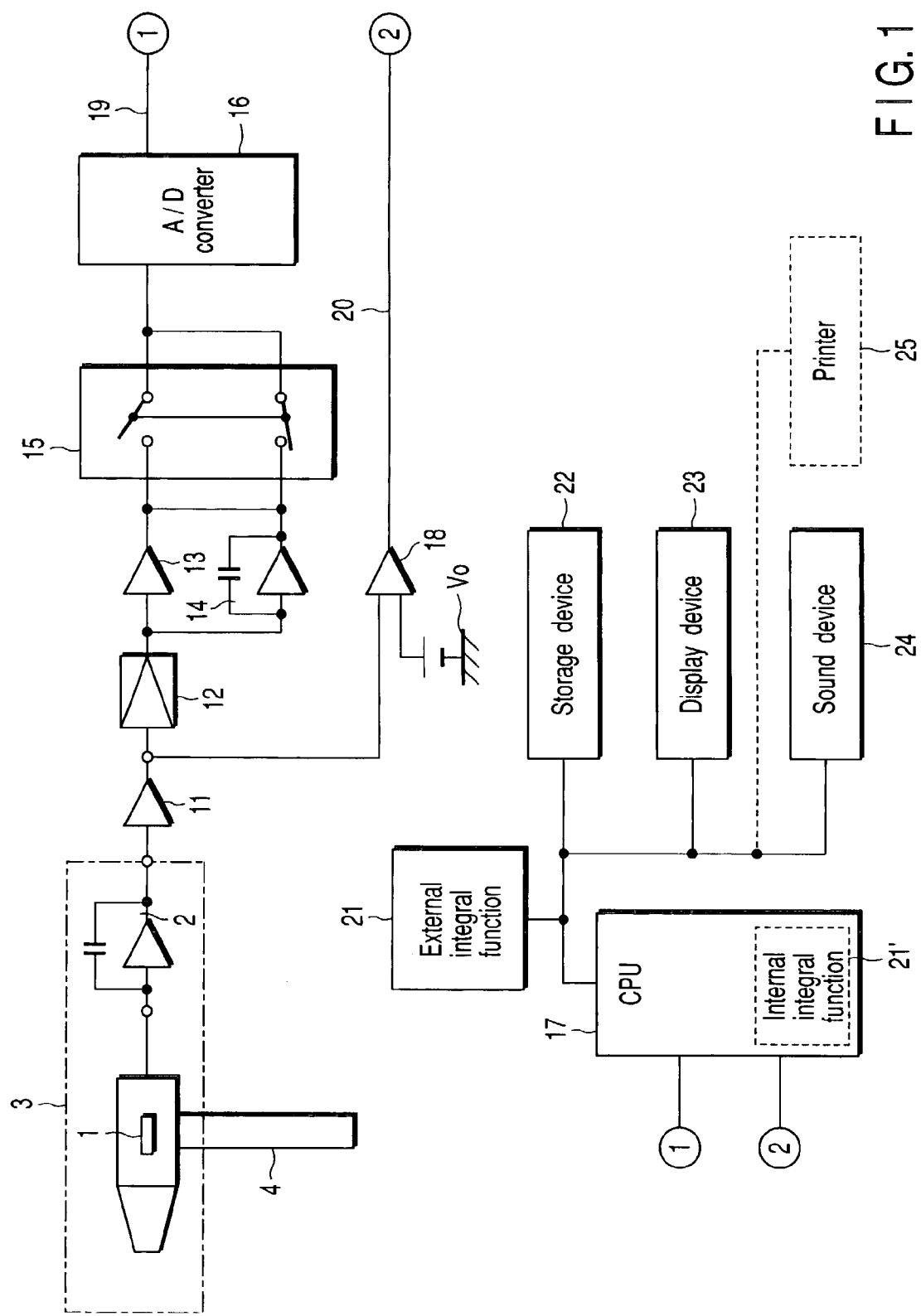
FIG. 1 is a circuit diagram of a conventional tooth mobility measuring apparatus.
Figure 3:
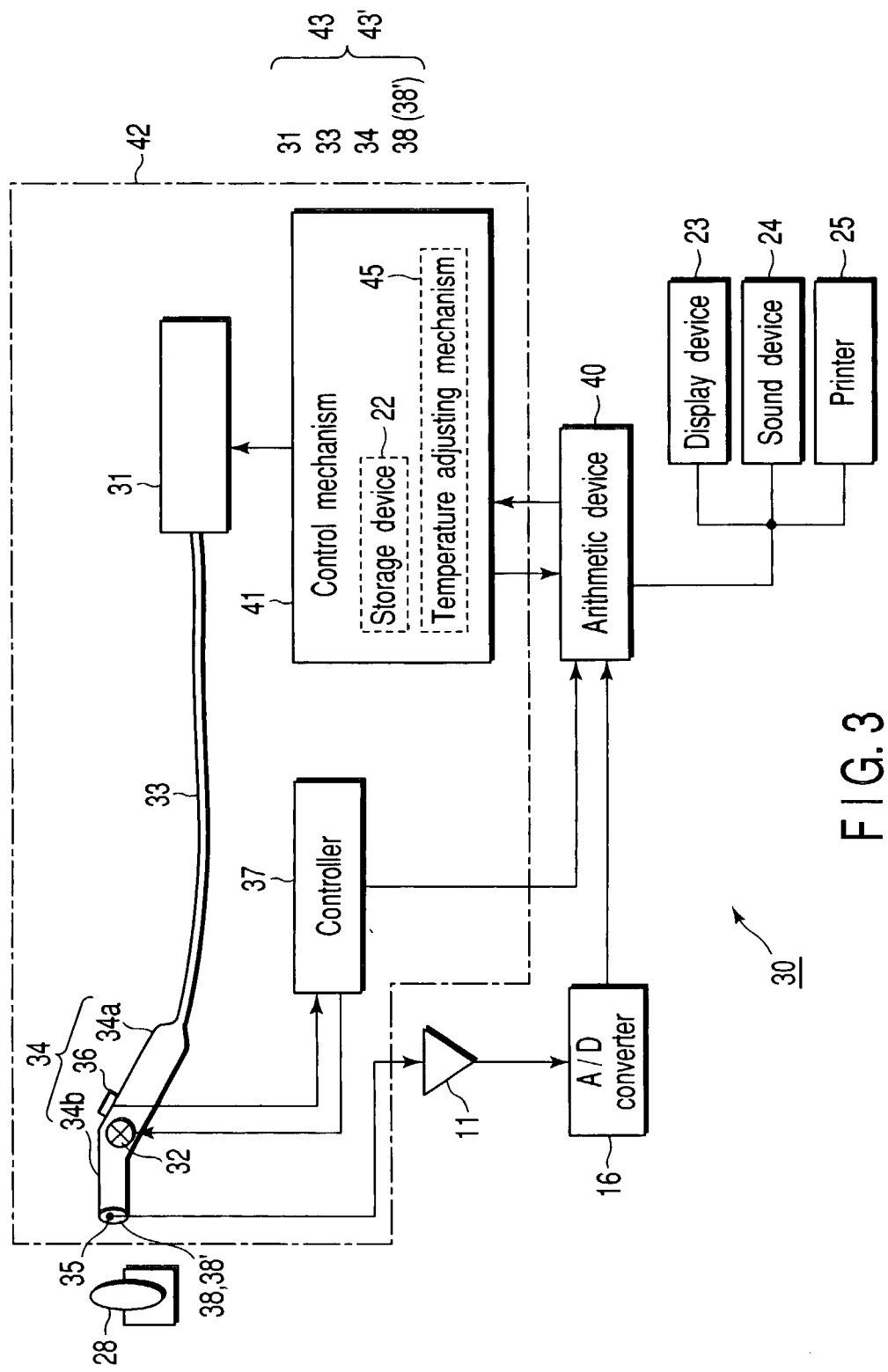
FIG. 3 is a view showing an embodiment of a tooth mobility measuring apparatus according to the present invention.

The present invention will be described below on the basis of an embodiment shown in FIGS. 3 to 5. Referring to FIG. 3, a tooth mobility measuring apparatus 30 comprises an impact mechanism 42 having an injection mechanism 43 with an injection port 38 for injecting a fluid (e.g., a liquid or a gas) to a tooth 28 or a suction mechanism 43' having a vacuum port 38' for sucking air, a sensor 35, and a tooth mobility calculation mechanism 44.

A case wherein the impact mechanism 42 has the injection mechanism will be described below. On the basis of this description, a person skilled in the art may also easily understand and practice a case wherein the impact mechanism has the suction mechanism.

The injection mechanism 43 may have a fluid compressor 31, a nozzle 34 which injects a fluid to a tooth, an elastic tube 33 which connects the fluid compressor 31 to the nozzle 34, and a control mechanism 41. A valve 32 may be arranged midway along the tube 33. The fluid injected by the injection mechanism 43 may be a gas, a liquid, or a mixture thereof.

A gas and, more particularly, air is preferably used from the viewpoint of ensuring easy handling and measuring accuracy. When a gas is used as the pressurized fluid, handling is easy. In addition, since the surface of the tooth may be kept in a state suitable for measurement, the measuring accuracy increases. When air is used as the pressurized fluid, no gas cylinder needs to be prepared, and no cost is required to prepare a specific gas such as nitrogen or carbon dioxide, resulting in advantage in terms of space and cost. On the other hand, when a liquid (e.g., water) is used as the pressurized fluid, handling is relatively easy, and a predetermined impact force may be ensured by injection at a pressure lower than that for a gas. The fluid injected by the injection mechanism 43 will be referred to as a gas hereinafter.

The fluid compressor 31 pressurizes the gas to a predetermined pressure and outputs the gas to the nozzle 34 through the tube 33. The tube 33 may have midway therealong the valve 32 which controls the flow of the pressurized gas. As the valve 32, any mechanism may be employed as long as it may be ON/OFF-controlled by hand or foot. For example, a solenoid valve may be employed as the valve 32. When the solenoid valve is employed, the operator may accurately and easily open/close the valve by ON/OFF-controlling a switch 36 disposed, near him or on the measuring apparatus main body, by hand or foot.

When the open/close speed, the open/close time, and the degree of open/close of the valve 32 are controlled to predetermined values by the electro-magnetic force, the stress form of the impact, i.e., the injection state of the injected gas (e.g., the pressure, injection amount, injection time) may be controlled. As the injection a pulsed or sinusoidally-varying injection may be employed. The switch may turn on/off a controller 37 for controlling the open/close of the valve 32.

The fluid compressor 31 may also have a temperature adjusting device which adjusts the temperature of the fluid to be output. The temperature adjusting device adjusts the gas to a predetermined temperature to prevent pain in the tooth caused by the temperature difference between the injected gas and the tooth.

The nozzle 34 injects the compressed gas output from the fluid compressor 31 to the tooth to be inspected through the valve 32. The nozzle 34 preferably has a structure that can make an operator easy to operate and can make an accurate gas injection to a tooth in the measurement. For this purpose, various shapes of nozzles may be employed. For example, to measure a front tooth, the distal end of the nozzle preferably has a straight shape, as shown in FIG. 3. On the other hand, to measure a back tooth, the distal end of the nozzle preferably has, e.g., an L shape.

Such shapes may be realized by exchanging the nozzle distal end portion in correspondence with the object to be inspected. Alternatively, the shapes may be realized by employing a nozzle distal end portion having a bendable structure. The shapes may be realized by covering the nozzle distal end portion with a cap having a predetermined shape. The nozzle 34 shown in FIG. 3 may be constituted by a grip portion 34a and distal end portion 34b. The grip portion may have the switch 36 which ON/OFF-controls the valve 32 or controller 37. The switch may be a foot switch. The valve 32 which turns on/off injection of the pressurized gas formed by the fluid compressor 31 and sent through the tube 33 may be arranged in the grip 34a. The valve 32 may be arranged in either the nozzle 34 or the tube 33. From the viewpoint of ensuring quick response of valve operation, the valve is preferably arranged at a position closer to the distal end portion 34b.

The distal end portion 34b of the nozzle 34 may have a tapered shape continuously from the grip 34a. The distal end portion may have the circular injection port 38, as shown in FIG. 4 or 5. A shape other than a circular shape may be employed for the injection port. For example, an injection port having a rectangular sectional shape may be employed for a front tooth, and an injection port having an elliptical sectional shape may be employed for a back tooth. As shown in FIG. 6, when a plurality of injection ports are prepared at the nozzle distal end portion, a plurality of teeth may be simultaneously measured.

The distal end portion 34b of the nozzle 34 may be integrated with the grip 34a. However, the distal end portion 34b may be detachably separated from the grip 34a. When the distal end portion 34b is separated, it may easily be detached from the grip 34a and subjected to a process such as cleaning. To change the sectional shape of the injection port of the nozzle and the shape of the nozzle distal end portion, the distal end of the nozzle may be covered with a cap having a predetermined structure.

The control mechanism 41 may control the pressure of the gas compressed by the fluid compressor 31 to a predetermined pressure. The predetermined pressure need not always be set to one value, and may be set to various pressure values in accordance with the state of the tooth, the age of the patient (adult or child), the purpose of inspection, and the like. To set the injection state of the gas to be injected from the valve 32 to a predetermined state, the controller 37 which ON/OFF-controls the valve 32 may adjust the number of times of injection, the injection timing, and the like. The controller 37 may be installed independently. Alternatively, it may be incorporated in the control mechanism 41.

The sensor 35 detects the movement of the tooth 28 that vibrates upon receiving an impact force from the gas injected from the distal end of the nozzle 34. An amplitude value as the displacement amount of the tooth, the period of vibration as the displacement time, the subsidence state of the vibration, or the like may be detected as the movement of the tooth. As for the sensor 35, a sensor which detects a change in air vibration such as a sonic wave or ultrasonic wave, or a change in electrostatic capacitance between the injection port and the tooth surface to detect the displacement state of the tooth may be used.

A sonic wave may suitably be used to detect a slow movement or very small fluctuation of a tooth. When a change in electrostatic capacitance is used, a simple sensor may be used, and the apparatus may easily be manufactured. A sensor using light is most preferable. In this case, a tooth is irradiated with light. The displacement state of the tooth may be detected on the basis of the phase shift or intensity of the reflected light.

A laser is preferably used as an incident light, though a light from a xenon lamp or LED may also be used. In this embodiment, a sensor using a laser (to be referred to as a "laser sensor" hereinafter) will be described. The laser sensor 35 may be arranged at the distal end of the nozzle 34 of the injection mechanism 43, as shown in FIG. 4. Alternatively, as shown in FIG. 5, the laser sensor 35 may be arranged at the outer periphery or inner periphery (not shown) of the nozzle 34. One or a plurality of sensors 35 may be arranged. When a plurality of sensors are arranged, different positions of a tooth to be inspected may be measured. Such measurement is useful to detect the three-dimensional variation of a tooth and diagnose a partial pathological portion. If a plurality of sensors are to be used, four sensors are preferably arranged from the viewpoint of increasing the reliability and accuracy of measurement.

A light from the sensor points a surface of the tooth under inspection. Hence, the position at which the fluid injected from the nozzle distal end is injected to the tooth may be visually recognized. According to the embodiment of the present invention, since the tooth need not be hit with a hammer, inspection may be done at an operator's desired position without causing any hammering position error due to a device movement.

FIG. 4 is a front view of the distal end portion of the nozzle 34. The injection port 38 which injects the gas is provided almost at the central portion of the distal end portion of the nozzle 34. The four laser sensors 35 may be arranged around the injection port. Each laser sensor 35 irradiates the tooth with a laser beam and receives the laser beam reflected by the tooth. When, for example, the phase of the laser beam with which the tooth is irradiated is compared with the phase of the received laser beam, the distance between the tooth and the sensor may be obtained on the basis of the phase shift. When the distance is obtained, the movement of the vibrating tooth may be detected. The obtained distance may also be used to calculate the degree of reduction of the pressure of the injected gas. The laser sensor may also obtain the distance from the intensity of the reflected light. The laser sensor may also detect the movement of the tooth on the basis of a change in intensity of reflected light.

A tooth mobility calculation mechanism (arithmetic device) 40 calculates the acceleration and tooth mobility when the tooth moves. Conventionally, the acceleration of a tooth that moves is measured by bringing the hammer distal end into direct contact with the tooth. According to the present invention, however, the acceleration may be calculated from the displacement amount and displacement time of a tooth without touching the tooth. Hence, operation error by the operator may be reduced, and a more accurate tooth mobility than that in the conventional apparatus may be calculated.

In this embodiment, the tooth vibrates upon receiving an impact from the pressurized gas injected from the nozzle 34. The displacement amount and displacement time of the tooth are measured by the sensor 35. Measurement data related to the tooth displacement measured by the sensor 35 is input to the arithmetic device 40 through an A/D converter 16. The arithmetic device calculates the A/D-converted measurement data to calculate the tooth mobility of the tooth. The tooth mobility calculation method will be described below.

Let F be the pressure of the fluid, $x$ be the displacement amount of the tooth, and $k$ be the modulus of elasticity of the gingiva. Then, they have a relation $$F = -k \cdot x \tag{1}$$

Since the pressure F has a known value, and the displacement amount $x$ is the measurement result, the modulus $k$ of elasticity may be obtained. However, the modulus $k$ of elasticity changes in accordance with the pressurizing position on the tooth. More specifically, as the pressurizing position separates from the root of tooth, the displacement amount increases, and therefore, the modulus $k$ of elasticity becomes small.

The time of vibration of the tooth, i.e., the displacement time is given by $$t = \pi (m/k)^{1/2} \tag{2}$$

where $t$ is the displacement time, and $m$ is the mass of the tooth and gingiva. The displacement time $t$ is obtained by measurement. The mass $m$ has a predetermined value for the same object to be inspected.

When equations (1) and (2) are combined, the modulus $k$ of elasticity is erased, and a relation $$x/t^2 = -F/m\pi^2 \tag{3}$$

is obtained. The left side of equation (3) indicates the acceleration. As is apparent from equation (3), the acceleration is proportional to the applied force F. Hence, the acceleration may be calculated from the displacement amount and displacement time.

As described above, to obtain the acceleration, the force applied to the tooth, i.e., the pressure value of the fluid is necessary. However, since the nozzle 34 which injects the fluid is separated from the tooth 28, the pressure of the injected fluid may decrease by some extent. To cope with this, in the present invention, the distance between the injection nozzle 34 and the tooth surface 28 is measured by a sensor in advance. Then, the pressure that is actually applied to the tooth may be calculated. The calculated pressure is evaluated together with the calculated acceleration, as described above, and expressed as a tooth mobility.

The calculated acceleration and tooth mobility of the tooth may be stored in a storage device 22 of the control mechanism 41 and also displayed on a display device 23. The tooth mobility of the tooth may also be printed on a paper sheet by a printer 25.

A method of measuring the tooth mobility of a tooth using the tooth mobility measuring apparatus 30 according to the embodiment of the present invention shown in FIG. 3 will be described. Referring to FIG. 3, a pressurized gas is formed by the fluid compressor 31. The pressure of the pressurized gas is controlled to a predetermined value by the control mechanism 41. The temperature of the pressurized gas is controlled to a predetermined value by a temperature adjusting mechanism 45. The operator brings the distal end portion 34b of the nozzle 34 close to the central portion of a tooth as an inspection object of a patient who is sitting on a chair. A portion to be measured on the tooth may be marked in advance. At this time, the distal end portion 34b of the nozzle 34 is preferably held at a right angle with respect to the central portion without touching the tooth to be measured.

As the position of the tooth to be inspected goes deep into the mouth, it becomes more difficult to locate the distal end of the nozzle at the central portion of the tooth. If a back tooth is to be measured, for example, the nozzle distal end portion may the covered with an L-shaped cap. In addition, when light is output from the sensor 35 arranged at the distal end portion 34b of the nozzle 34, the impact position of the fluid injected from the nozzle 34 may be visually recognized. Hence, even for a tooth such as a back tooth that is hard to inspect, the injection port may easily be located to face the tooth to be inspected.

The operator operates the switch 36 on the nozzle 34 by hand or a foot switch to turn it on. With this switching, control by the controller 37 starts, and the valve 32 in the nozzle 34 opens/closes in a predetermined way. While the valve 32 is open in a predetermined way, the gas sent from the fluid compressor 31 trough the tube 33 is injected from the injection port 38 of the nozzle 34 to the central portion of the tooth in, e.g., a pulse-like pattern.

The tooth moves upon injection. The sensor 35 detects predetermined items such as the maximum displacement amount and displacement time of the moving tooth and the distance from the injection port 38 to the tooth to be inspected. The pieces of detected information are amplified by an amplifier 11, converted into digital data by the A/D converter 16, then input to the arithmetic device 40. The arithmetic device may also receive the pressure information of the pressurized gas or the distance between the nozzle and the tooth from the control mechanism 41 or data related to the gas injection state from the controller 37. The arithmetic device 40 calculates the tooth mobility on the basis of the input data. The tooth mobility as the measurement result may be stored in the storage device 22 of the control mechanism 41 or displayed on the display device 23 as a numerical value or a graph. The measurement result may also be printed on a paper sheet by the printer 25, as needed. Alternatively, the result may be output as sound by a sound device 24.

The tooth mobility of the tooth may be measured in the above-described manner. This measurement may be executed for one tooth either once or a plurality of times. When the measurement is executed a plurality of times, a plurality of measurements may be executed in a short time by causing the controller 37 to intermittently continuously open/close the valve 32. When the measurement is executed a plurality of times, the same pressurized gas injection condition may be applied each time. Alternatively, the pressurized gas injection condition may be automatically changed every time by the controller 37. When measurement is executed while changing the pressurized gas injection condition every time, the tooth mobility may be measured by selecting the optimum condition for the tooth from the different conditions. The above-described inspection method may be executed not only for one tooth but also simultaneously for a plurality of teeth. Even, e.g., an artificial tooth fixed by a bridge may also be simultaneously inspected.

When the above tooth mobility measuring operation is performed, the tooth mobility measuring apparatus 30 may have a notification mechanism (sound device 24) which notifies the operator of the end of measurement by, e.g., sound (e.g., beep). If the notification mechanism outputs no sound that indicates the end, the operator may easily recognize that the measurement is not ended yet and decide to start measurement again.

According to the embodiment of the present invention, when a fluid is used, a tooth may be moved without directly touching it. When a fluid is used, the impact force to be applied to the tooth may have an accurate value. In addition, by the method of calculating the acceleration, the tooth mobility may be measured without bringing the sensor into contact with the tooth. Since the apparatus need not be brought into direct contact with the tooth, it may easily be disinfected, unlike the conventional apparatus that requires sterilization.

In the embodiment of the present invention, the pressure of the pressurized fluid to be injected or the pressure of suction may be adjusted by the controller 37. When a tooth with high tooth mobility is to be inspected, the pressure may be reduced. Hence, the measurement may be executed while easing the pain on the patient. In addition, the temperature of the pressurized fluid may also be adjusted. Hence, the measurement may be executed while easing the pain or discomfort of the patient.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A tooth mobility measuring apparatus comprising:
    an impact mechanism which has at least one of an injection mechanism having an injection port which injects a fluid and a suction mechanism having a vacuum port which sucks air, and applies directly an impact force on a tooth by injection of the fluid or suction of air, the impact mechanism comprising a control mechanism which sets a pressure by injection or suction to a predetermined value;
    at least one sensor which detects a displacement state of the tooth which is moved by the impact force of the impact mechanism; and
    a tooth mobility calculation mechanism which calculates a tooth mobility of the tooth on the basis of an output signal from the sensor.

2. An apparatus according to claim 1, wherein the fluid injected by the injection mechanism is a gas.

3. An apparatus according to claim 1, wherein the injection port which injects the fluid or the vacuum port which sucks air has a structure capable of simultaneously measuring a plurality of teeth.

4. An apparatus according to claim 1, wherein the control mechanism may adjust the predetermined value.

5. An apparatus according to claim 1, wherein the injection mechanism may adjust at least one of an injection state, a number of times of injection, and an injection timing of the fluid to be impactively injected to the tooth to be inspected.

6. An apparatus according to claim 1, wherein the sensor is a measuring device which irradiates the tooth with light and detects the displacement state of the tooth on the basis of reflected light.

7. An apparatus according to claim 6, wherein the light output from the sensor also has a position confirming function to visually recognize a position of a target to be subjected to injection or suction by the impact mechanism.

8. An apparatus according to claim 1, wherein the sensor is arranged around the injection port or the vacuum port.

9. An apparatus according to claim 1, wherein the displacement state of the tooth to be detected is at least one of a displacement amount and a displacement time of the tooth to be inspected.

10. An apparatus according to claim 1, wherein the tooth mobility calculation mechanism calculates an acceleration of displacement of the tooth on the basis of a maximum displacement amount and a displacement time of the tooth to be inspected.

11. An apparatus according to claim 1, wherein the apparatus further comprises means for locating the injection port or the vacuum port with respect to the tooth to be inspected.

12. A tooth mobility measuring method comprising:
    (a) applying an impact force having a predetermined pressure on a tooth to be inspected, the impact force being applied by one of injecting a fluid having a predetermined pressure to the tooth to be inspected and sucking the tooth to be inspected at a predetermined pressure;
    (b) detecting a displacement state of the toot which is moved by the impact force; and
    (c) calculating a tooth mobility of the tooth on the basis of the detected displacement state.

13. A method according to claim 12, wherein the fluid in the applying an impact force is a gas.

14. A method according to claim 12, wherein the applying an impact force further comprises a step of adjusting the impact force.

15. A method according to claim 12, wherein the detecting a displacement state of the tooth comprises a step of adjusting at least one of the stress form of the impact, a number of times of impact, and a timing of application of the impact force.

16. A method according to claim 12, wherein the applying an impact force further comprises a step of locating an injection port or a vacuum port at a predetermined position using means for locating the injection part or the vacuum port with respect to the tooth to be inspected.

17. A method according to claim 12, wherein the detecting a displacement state of the tooth comprises a step of irradiating the tooth with light and detecting the displacement state of the tooth on the basis of reflected light.

18. A method according to claim 12, wherein the detecting a displacement state of the tooth comprises a step of detecting the displacement state of the tooth from at least one of a displacement amount and a displacement time of the tooth to be inspected.

19. A method according to claim 12, wherein the calculating a tooth mobility of the tooth on the basis of the detected displacement state comprises a step of calculating the tooth mobility of the tooth on the basis of at least one of the impact force applied to the tooth to be inspected, a maximum displacement amount of the tooth, a displacement time of the tooth, and a distance between an injection port or a vacuum port and the tooth to be inspected.

20. An apparatus according to claim 1, further comprising a nozzle which has at least one of an injection port which injects a fluid and a vacuum port which sucks air, wherein at least one of the injection port and the vacuum port is capable of applying an impact force on at least one tooth.

* * * * *